US009295803B2

(12) United States Patent
Korten

(10) Patent No.: US 9,295,803 B2
(45) Date of Patent: Mar. 29, 2016

(54) VENTILATOR SYCHRONIZATION INDICATOR

(75) Inventor: Jerome B. Korten, New York, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 849 days.

(21) Appl. No.: 13/600,835

(22) Filed: Aug. 31, 2012

(65) Prior Publication Data
US 2014/0060539 A1 Mar. 6, 2014

(51) Int. Cl.
A61M 16/00 (2006.01)
A61M 16/10 (2006.01)
A61M 16/12 (2006.01)
A61M 16/08 (2006.01)
A61M 16/16 (2006.01)
A61M 16/22 (2006.01)
A61B 5/087 (2006.01)

(52) U.S. Cl.
CPC .......... A61M 16/12 (2013.01); A61M 16/0051 (2013.01); A61B 5/087 (2013.01); A61B 2562/0247 (2013.01); A61M 16/0808 (2013.01); A61M 16/0866 (2014.02); A61M 16/16 (2013.01); A61M 16/22 (2013.01); A61M 2016/0015 (2013.01); A61M 2016/0027 (2013.01); A61M 2016/0036 (2013.01); A61M 2016/1025 (2013.01); A61M 2202/0208 (2013.01); A61M 2205/3331 (2013.01); A61M 2205/502 (2013.01); A61M 2205/52 (2013.01); A61M 2205/80 (2013.01)

(58) Field of Classification Search
CPC ................ A61M 16/0051; A61M 2202/0208; A61M 2205/80; A61M 2216/1025; A61M 16/0866; A61M 16/0808; A61M 16/22; A61M 16/16; A61M 2016/0036; A61M 2016/0027; A61M 2016/0015; A61M 2205/3331; A61M 5/087; A61M 2562/0247
See application file for complete search history.

(56) References Cited

U.S. PATENT DOCUMENTS

| 5,520,192 | A | * | 5/1996 | Kitney et al. ................. 600/529 |
| 5,740,797 | A | | 4/1998 | Dickson | |
| 6,148,814 | A | * | 11/2000 | Clemmer et al. ........ 128/200.24 |
| 6,431,171 | B1 | | 8/2002 | Burton | |
| 7,484,508 | B2 | * | 2/2009 | Younes .................... 128/204.18 |
| 7,819,815 | B2 | | 10/2010 | Younes | |
| 2002/0053345 | A1 | * | 5/2002 | Jafari et al. ............... 128/204.23 |
| 2009/0205654 | A1 | * | 8/2009 | Bouillon et al. ......... 128/203.12 |
| 2009/0240126 | A1 | * | 9/2009 | Baker et al. ................... 600/324 |

FOREIGN PATENT DOCUMENTS

| WO | 98/41146 A1 | 9/1998 |
| WO | 2006/043278 A1 | 4/2006 |
| WO | 2011/141843 A1 | 11/2011 |

OTHER PUBLICATIONS

Letellier, C., Rabarimanantsoa, H., Achour, L., Cuvelier, A., Muir, J-F., Recurrence Plots for Dynamical Analysis of Non-Invasive Mechanical Ventilation, Philosophical Transactions of The Royal Society, 2008, pp. 621-634, The Royal Society, France.

(Continued)

Primary Examiner — Justine Yu
Assistant Examiner — Douglas Sul

(57) ABSTRACT

A method and apparatus determine a phase angle between a first signal based on ventilator airflow for a breath and a second signal based upon ventilator firing for the breath. Based on the phase angle, an indication of a nature of dissynchrony of airflow and ventilator firing is provided.

17 Claims, 5 Drawing Sheets

(56) References Cited

OTHER PUBLICATIONS

Louren, M.S., Van Den Berg, B., Aerts, J.G.J.V., Verbraak, A.F.M., Hoogsteden, H.C., Bogaard, J.M., Expiratory Time Constants in Mechanically Ventilated Patients With and Without COPD, Intensive Care Med, Oct. 31, 2000, 7 pages, vol. 26, Springer-Verlag, Rotterdam, Netherlands.

Rabarimanantsoa, H., Achour, L., Letellier, C., Cuvelier, A., Muir, J-F., Recurrence Plots and Shannon Entropy for a Dynamical Analysis of Asynchronisms in Noninvasive Mechanical Ventilation, Mar. 21, 2007, 10 pages, vol. 17, American Institute of Physics, France.

European Search Report and Written Opinion issued in connection with EP Application No. 13179682.3 on Dec. 16, 2013.

* cited by examiner

VENTILATOR SYCHRONIZATION INDICATOR

BACKGROUND

Ventilators are machines used to assist or replace spontaneous breathing of a patient. In some circumstances, a ventilator may also be used to supply anesthetic agents to the patient undergoing certain medical procedures. With existing ventilators, monitoring patient breathing and ventilator performance may be difficult. A caretaker may not easily determine whether a patient is struggling to breathe, whether a patient is fighting the assistance of the ventilator or whether the ventilator is optimally operating to assist the patient with his or her breathing.

DETAILED DESCRIPTION OF THE EXAMPLE EMBODIMENTS

Figure 1:
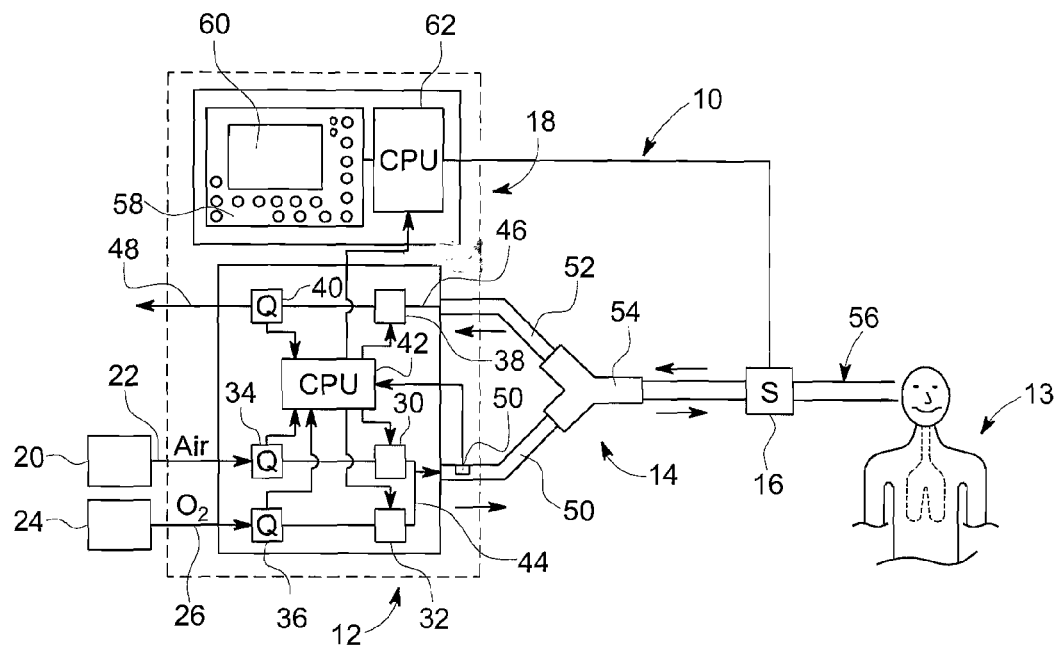
FIG. 1 is a schematic illustration of an example mechanical ventilation system.

FIG. 1 schematically illustrates an example of a mechanical ventilation system 10. Ventilation system 10 provides a pneumatic circuit that carries breathing gas to and exhaled air from a patient 13 to assist patient 13 in breathing. As will be described hereafter, ventilation system 10 provides a graphic that allows a caretaker to more quickly and easily monitor patient breathing and ventilator performance. Ventilation system 10 enables a caretaker to more easily determine whether a patient is struggling to breathe, whether a patient is fighting the assistance of the ventilator or whether the ventilators optimally operating to assist the patient with his or her breathing. Ventilation system 10 comprises ventilator 12, breathing circuit 14, sensor 16 and display and control unit 18.

Ventilator 12 supplies gas, such as air or air including anesthetics, drugs or the like, to patient 13 through breathing circuit 14 and receives exhaled air through breathing circuit 14. In the example illustrated, ventilator 12 receives air from air source 20 through conduit 22 and receives oxygen ($O_2$) from an oxygen source 24 (such as a container of compressed oxygen) through conduit 26. Ventilator 12 comprises valves 30, 32, sensors 34, 36, valve 38 and sensor 40 and controller or processing unit 42. Valves 30, 32 control a supply of air and oxygen (the mixture thereof), respectively, through conduit 44 to breathing circuit 14. Sensors 34 and 36 sense or detect the supply of the air and oxygen, respectively, and transmit signals representing such sensed values to processing unit 38.

Valve 38 comprises a valve mechanism connected to breathing circuit 14 by conduit 46 so as to control the flow of exhaled air received from breathing circuit 14 to the discharge conduit 48. Sensor 40 comprises a device to sense the flow of exhaled air to discharge port 48. Such sensed values for the exhaled air are further transmitted to controller or processing unit 38.

Processing unit 42 generates control signals controlling the operation of valves 30, 32 and 38. For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, processing unit 42 (CPU) may be embodied as part of one or more application-specific integrated circuits (ASICs). Unless otherwise specifically noted, the controller is not limited to any specific combination of hardware circuitry and software, nor to any particular source for the instructions executed by the processing unit. In other implementations, processing unit 42 may be included as part of one or more processing units associated with display control unit 18.

Breathing circuit 14 delivers breathing gas (air, oxygen and possibly other additives such as anesthetics, medicines and the like) from ventilator 12 to patient 13 while also directing exhaled air from patient 13 to system 10 and ventilator 12. Breathing circuit 14 comprises inspiratory section or segment 50, expiration segment 52, Y connector 54 and patient segment 56. Inspiratory segment 50 extends from and is pneumatically connected to conduit 44 at one end and Y connector 54 at the other end. Segment 50 delivers gases from conduit 44 to patient segment 56 during forced, assisted or voluntary inhalation by patient 13. Exhalation segment 52 delivers exhaled gases are exhaled air from patient segment 56 to conduit 46. Y connector 54 connects each of segments 50 and 52 to patient segment 56. Patient segment 56 extends from Y connector 54 to patient 13. Patient segment 56 may include devices for pneumatically connecting with patient 13 such as through the nose, mouth or trachea of patient 13.

During inspiration (inhalation), breathing air is delivered through patient segment 56 and into the lungs of patient 13. During expiration or exhalation, expired or exhaled breathing air exits the lungs the patient 13 and is received into patient segment 56. The expired breathing air is communicated or transmitted through patient segment 56, through Y connector 54 and into expiration segment 52. Although not illustrated, in other implementations, ventilation system 10 may comprise additional devices or systems. For example, in one implementation, system 10 may additionally include a nebulizer positioned between ventilator 12 and inspiratory section 50 to introduce a medical drug or anesthetic agent to breathing air for the patient. In yet other implementations, breathing circuit 14 may comprise a component such as a humidifier to humidify the breathing air, a heater to heat the breathing air or a water/vapor trap to remove excess moisture from a particular segment or section of ventilation system 10.

In some implementations, ventilator 12 may additionally include a carbon dioxide scavenger which removes carbon dioxide from exhaled air and returns or recycles the air by conducting such recycled air to conduit 22. In one implementation, ventilator 12 utilizes a bellows to pressurize air being supplied to conduit 50. For example, in one implementation, ventilator 12 selectively supplies and withdraws pressurized air to and from an exterior of a bellows assembly. During inhalation, ventilator 12 supplies gas or air to the exterior of the bellows, collapsing the bellows to force gas within bellows to through the carbon dioxide scavenger and to the breathing circuit 14 and the patient's lungs. During exhalation, expelled gas from the patient's lungs passes through valve 38 to fill the bellows. In other implementations, the noted carbon dioxide scavenger as well as the bellows may be omitted.

Sensor 16 comprise a device configured to sense or detect pressure and/or flow of air (with or without additives) corresponding to forced, voluntary or assisted inhalation and exhalation by patient 13. In the example illustrated, sensor 16 is located within patient segment 56. In other implementations, sensor 16 may be provided at other locations. For example, in other implementations, sensor 16 may be provided as part of a mouthpiece through which patient 13 inhales and exhales.

Figure 1A:
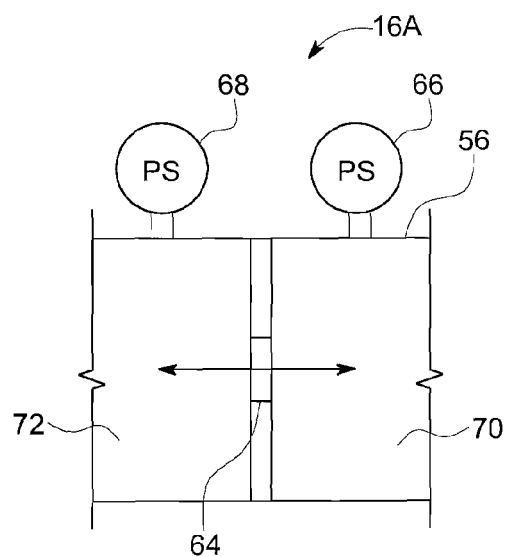
FIG. 1A is a fragmentary schematic illustration of an example sensor of the system of FIG. 1.

FIG. 1A illustrates sensor 16A, one example of sensor 16. As shown by FIG. 1A, sensor 16A comprises a pneumotachometer which senses pressures on opposite sides of a flow resister and utilizes a pressure gradient to determine flow and direction. In the example illustrated, sensor 16A includes a flow resister passage 64 and pressure transducers or sensors 66, 68. Flow resister passage 64 comprise a constriction through which gas or air flows, causing pressure buildups on either side of passage 64 depending upon the direction of airflow. Flow resister passage 64 divides patient segment portion 56 into a patient side 70 and a ventilator side 72 of resistive flow passage 64. Pressure sensor 66 senses a patient side pressure while pressure sensor 68 senses a ventilator side pressure. Such pressure signals are transmitted or communicated to display and control unit 18.

Display and control unit 18 receives signals from sensor 16 and provides a visible graphical indication of a nature of dis-synchrony of patient generated airflow and ventilator operation. Display and control unit 18 utilizes such signals to determine a phase angle based relationship between an input based on airflow for a breath and input based upon ventilator firing for the breath. For purposes of this disclosure, the phrase "based on airflow for a breath" or "based on airflow in a ventilator for a breath" shall mean a signal or input that has a relationship to airflow for a breath or breathing. Such a signal or input may comprise signals pertaining to a sensed pressure or sensed pressure differentials in a passage. For example, a patient's breathing will create airflow in a passage, wherein such airflow will create pressure differentials across a pneumotachometer and wherein signals from the pneumotachometer are signals based upon such airflow. For purposes of this disclosure, the phrase "based upon ventilator firing for the breath" shall mean an input or signal that has a relationship to the firing of the ventilator for a breath. Such an input or signal may comprise sensed pressure or sensed pressure differentials in a passage which may occur as a result of the firing of a ventilator. The phase angle based relationship is used to generate the graphical indication of dis-synchrony. The graphical or visually discernible indication of dis-synchrony allows a physician or caretaker to quickly and easily determine, at a glance, the relationship between the patient's breathing in the operation of the ventilator.

Display control unit 18 comprises inputs 58, display 60 and control unit 62. Inputs 58 comprise one or more devices by which a physician or caretaker may enter or input commands, instructions or selections for mechanical ventilation system 10. In one implementation, input 58 comprise a series or arrangement of knobs, buttons, dials, toggle switches, rocker switches and the like. In one implementation, input 58 may alternatively or additionally include a keyboard, a touchpad, a microphone associated with speech recognition software, a stylus, and a touch screen. In one implementation, the touch screen may be incorporated as part of display 60.

Display 60 comprises a monitor, screen or panel by which graphics and text may be visibly displayed for viewing by a physician or caretaker. In one implementation, display 60 may comprise an light emitting diode screen. In other implementations, display 60 may utilize other display technologies. In the example illustrated, inputs 58 and display 60 are illustrated as being integral are as part of system 10. In other implementations, inputs 58 and display 60 may be provided part of a separate electronic device, such as a separate portable electronic device, wherein signals from the separate electronic device are transmitted to and received by control unit 62 of system 10. For example, display 60 and inputs 58 may alternatively incorporate as a portable electronic device such as a personal data assistant, flash player, tablet computer, laptop computer in the like.

Control unit 62 comprises one or more processing units configured to receive signals from processing unit 42 for analysis and the presentation of information on display 60, to generate control signals which are transmitted to controller 42 based upon inputs or selections received through input 58, and to receive signals from sensor 16 to generate control signals for directing display 60 to present a visible graphical indication of a nature of dis-synchrony of patient generated airflow and ventilator operation. Control unit 62 follows directions or instructions, such as software or code, contained in one or more non-transient computer-readable mediums or persistent storage devices. In some implementations, control unit 62 may be located remote from ventilator 12, wherein such control signals and analysis are performed remotely from ventilator 12, such as through cloud computing.

Figure 2:
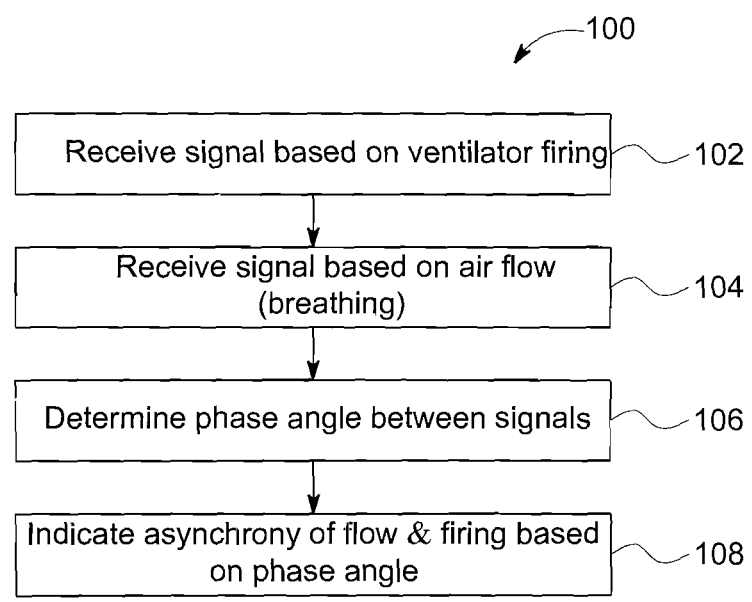
FIG. 2 is a flow diagram of an example method that may be carried out by the system of FIG. 1.
Figure 3:
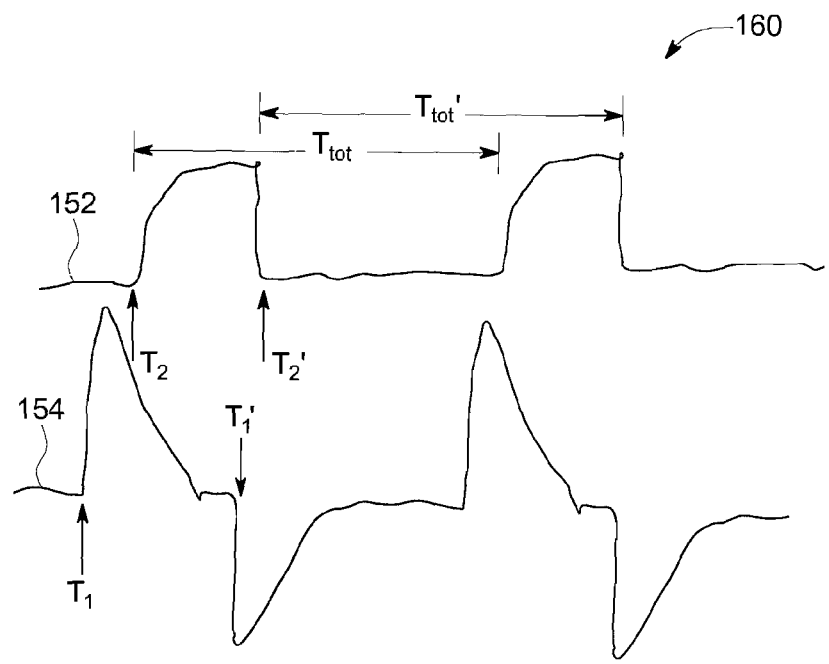
FIG. 3 is a diagram illustrating signals and values derived from signals from a first example ventilator synchrony scenario and used by the system of FIG. 1 in carrying out the method of FIG. 2.

FIG. 2 is a flow diagram of an example method 100 which may be carried out by system 10. FIG. 3 illustrates an example set of signals or values derived from signals from sensor 16 (or sensor 16A) utilized in method 100. As indicated by step 102, control unit 62 receive signals from sensor 16 based on ventilator airflow/pressure. In one example where sensor 16A is employed, control unit 62 receives signals from pressure sensor 68, the pressure sensor in patient segment 56 on ventilator side 72. Line 152 in FIG. 3 represents an example series of signals received by control unit 62 from pressure sensor 68 over time. Upward spikes in line 152 indicating increasing pressure on ventilator side 72 of resistive passage 64 as detected by pressure sensor 68. Such upward spikes in line 152 indicate firing or initiation by ventilator 12, wherein ventilator 12 supplies and directs pressurized gas towards the patient 13, increasing the pressure on ventilator side 72.

As indicated by step 104, control unit 62 also receives signals from sensor 16 (sensor 16A) based on or representing airflow (or patient initiated breathing in some circumstances). As shown by FIG. 3, the lower line 154 represents air flow and air flow direction which correspond to pressure gradient between sensors 66 and 68, wherein the upward direction occurs when the sensed pressure at sensor 68 is greater than the sensed pressure at sensor 66 and wherein a downward direction occurs when the pressure at sensor 68 is less than the sensed pressure at sensor 68. In other words, the upward spikes of line 154 occur when a patient is initiating a breath such that the pressure at sensor 68 is greater than the sensed pressure at sensor 66. The downward spikes of line 154 occur when a patient is exhaling and ventilator 12 is no longer supplying pressurized air such that the sensed pressure at sensor 66 is greater than the sensed pressure at sensor 68.

As indicated by step 106 in FIG. 2, control unit 62 utilizes such sets of signals or inputs to determine a phase angle for each breath (inhalation period) based on a relationship between the ventilator firing input and the airflow/breathing input. Control unit 62 determines a phase angle based on a relationship between the upward spikes in line 154 (patient initiated breathing) and the upward spikes in line 152 (ventilator firing initiation) to generate a graphical display illustrating a nature of any dis-synchrony between such breathing our airflow and ventilator firing. In particular, a cycle or Ttot of 2 Pi radians is defined by the time between consecutive ventilator firing peaks in line 152. The phase angle for an individual breath is determined according to the equation: phase angle=2 Pi(T2−T1)/Ttot, where time T2 is the time at which ventilator 12 is fired (represented by the upward spike in line 152) and where time T1 is a time at which a patient begins to inhale to initiate the breath (represented by spike in line 154).

Figure 4:
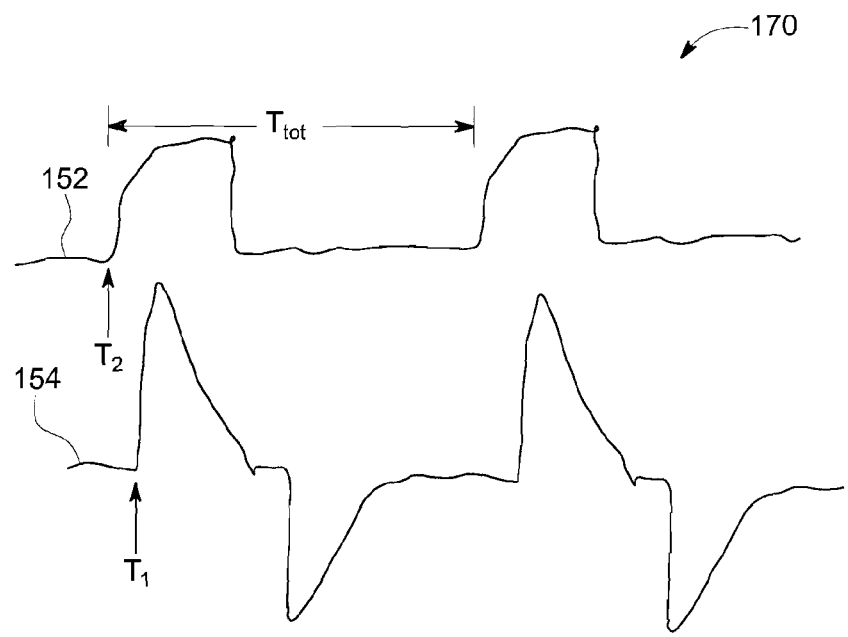
FIG. 4 is a diagram illustrating signals and values derived from signals from a second example ventilator synchrony scenario and used by the system of FIG. 1 in carrying out the method of FIG. 2.

FIGS. 3 and 4 illustrate two alternative scenarios where the calculated phase angle is positive and is negative. FIG. 3 illustrates scenario 160 where the patient's initiation of a breath leads the firing of ventilator 12. As shown by FIG. 3, the time at which the patient initiates a breath (time T1) perceive the time at which the ventilator is fired (T2). As a result, the phase angle is positive.

FIG. 4 illustrates an alternative scenario 170, wherein the pressurized air being supplied by ventilator 12 is fired at time T2 which precedes the time at which the patient begins breathing as indicated by lower line 154 at time T1. As shown by FIG. 4, the time at which the patient initiates a breath (time T1) succeeds or follows the time at which the ventilator is fired (time T2). As a result, the phase angle is negative. In other implementations, the phase angle may be calculated in other fashions.

As indicated by step 108 in FIG. 2, upon calculating the phase angle, control unit 62 utilizes the calculated phase angle for the breath to graphically or visibly indicate asynchrony or dis-synchrony between gas or airflow and ventilator firing. In particular, control unit 62 utilizes the calculated phase angle to generate one or more graphics, icons or marks which are displayed on display 60 in which visually indicate such dis-synchrony. As a result, a caretaker or physician may quickly and easily visibly determine the relationship between the initiation of breathing by a patient and the time at which ventilator 12 is fired to assist such breathing. Based upon a physical determination, the caretaker or physician may then make adjustments to the operation of ventilator 12 through input 58 to enhance the performance of ventilator 12 to address the breathing characteristics of patient 13.

Figure 5:
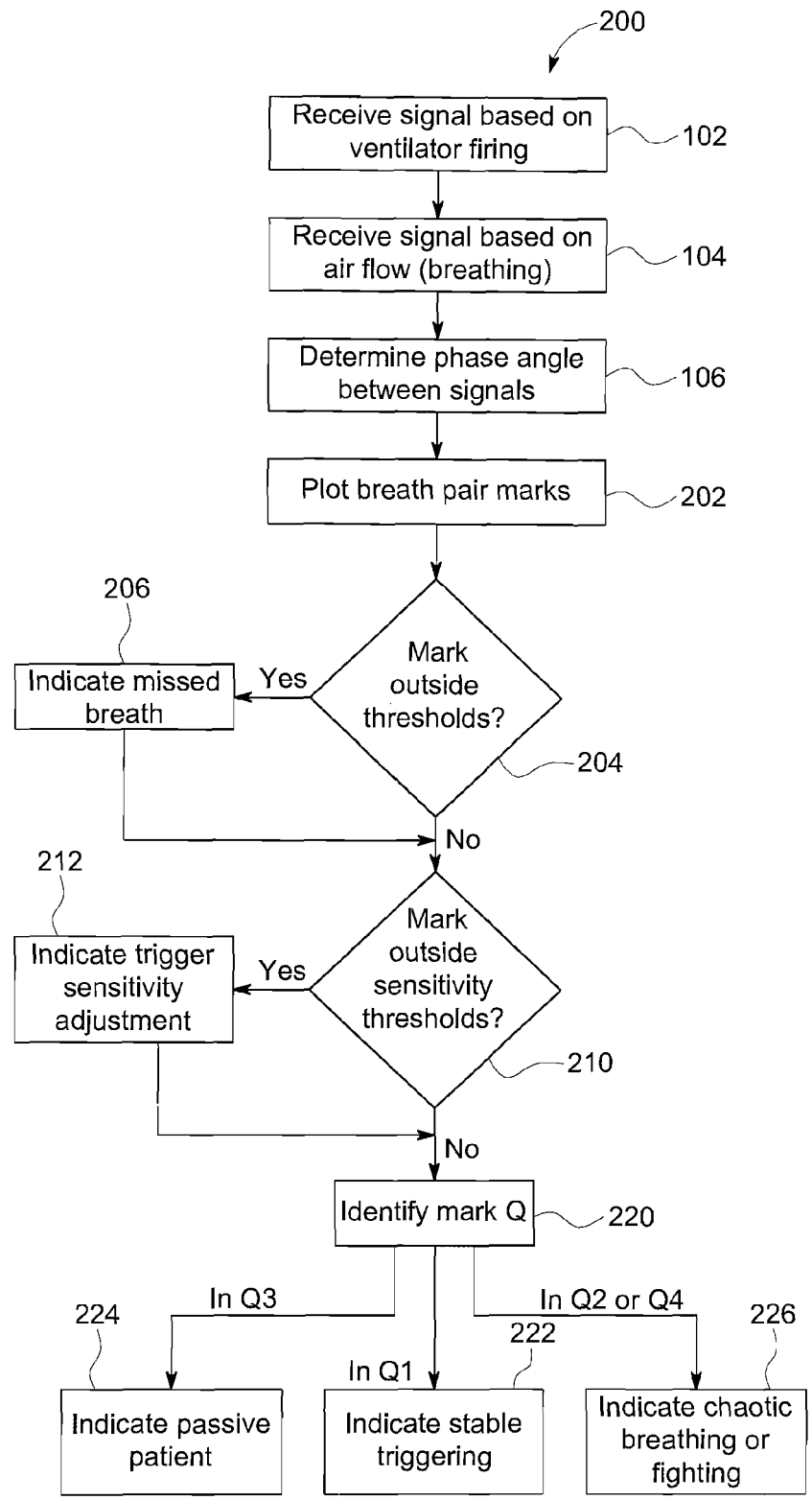
FIG. 5 is a flow diagram of another example method that may carried out by the system of FIG. 1.
Figure 6:
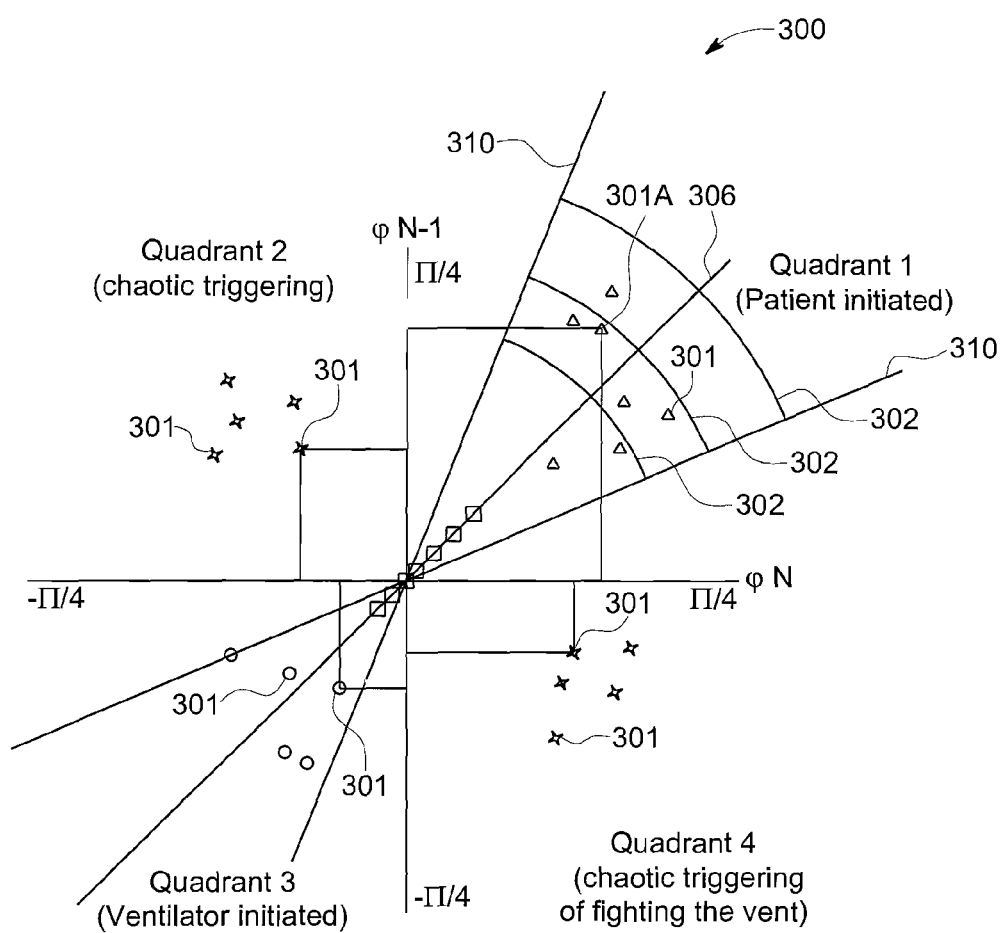
FIG. 6 is a diagram of an example display that may be presented by the system of FIG. 1.

FIGS. 5 and 6 illustrate a particular example method 200 and display presentation 300, respectively, for visibly representing the relationship between the initiation of breathing by patient 13 and the time at which ventilator 12 is fired using the aforementioned calculated phase angles. As shown by FIG. 5, steps 102, 104 and 106 correspond to such steps described above with respect to method 100. As indicated by step 202, control unit 62 plots consecutive breath pair marks 301. As shown by FIG. 6, a calculated phase angle for a first breath of a consecutive pair of breaths determines the y-axis coordinate or value for the breath pair mark 301A and the calculated phase angle for a second breath of the consecutive pair of breaths determines the x-axis coordinate or value for the breath pair mark 301A. As shown by FIG. 6, a first breath having a positive phase angle and a second breath also having a positive phase angle, forming a first pair of breaths, will result in the plotting of a first mark 301 (illustrated with a triangle for ease of discussion) in quadrant 1. A third breath having a negative calculated phase angle, forming a second breath pair with the second breath, will result in the plotting of a second mark 301 (illustrated with a star) in quadrant 2. A fourth breath having a negative calculated phase angle, forming a third breath pair with the third breath, will result in the plotting of a third mark (illustrated with a circle) in quadrant 3. A fifth breath having a positive calculated phase angle and forming a fourth pair with the fourth breath result in the plotting of a fourth mark (illustrated with a star) in quadrant 4. Each breath forms the y-axis coordinate for a first breath pair mark and the x-axis coordinate for a second breath pair mark.

In one implementation, the plotting of breath pair marks shown in FIG. 6 is presented on display 60 by control unit 62. Visual inspection of the quadrant in which a particular breath pair mark lies as well as its relationship to the origin (x=0, y=0) provides the caretaker or physician with immediate information as to the synchrony or dis-synchrony between patient breathing and ventilator firing. For example, breath pair marks plotted in quadrant 1 reflect patient initiated breathing, wherein a patient 13 starts to breathe (starts to inhale) and ventilator 12 responds by firing to supply pressurized air/gas to assist patient 13 with the breath or inhalation.

The spacing of the breath pair mark from the origin indicates how responsive ventilator 12 is to the patient's initiation of a breath. For example, breath pair marks closer to the origin reflect a more responsive ventilator 12 while breath pair marks farther away from the origin reflect a more insensitive ventilator 12. A majority of breath pair marks spaced from the origin by a large distance may indicate the need to adjust and increase a sensitivity of ventilator 12 such that ventilator 12 more quickly responds to the initiation of a breath by patient 13. In some circumstances, the majority of breath pair mark spaced from the origin by large distance may indicate the need to replace the current ventilator with a more sensitive ventilator or a more sensitive ventilator component for enhanced responsiveness.

In the example illustrated, control unit 62 visibly displays or depicts a threshold with respect to the origin beyond which a breath pair mark is deemed to suggest the adjustment of ventilator trigger sensitivity. In the example illustrated, such thresholds are depicted by one or more radial trigger sensitivity threshold lines 302, wherein different threshold lines reflect different suggested or recommended degrees of adjustment for trigger sensitivity of ventilator 12. In other implementations, such trigger sensitivity threshold lines 302 may be omitted, wherein control unit 62 performs an internal comparison with a predefined thresholds and wherein different breath pair marks are illustrated are depicted with different characteristics depending upon their relationship to the predefined thresholds. For example, breath pair marks beyond a certain threshold may have one or more of a different color, a different brightness, a different size, a different flashing or flashing frequency, a different shade and the like with respect to other breath pair marks which do not lie beyond the predefined threshold. In some implementations, line 302 may be employed with the provision of different characteristics for different breath pair marks based on their relationship to the threshold or relationship to the origin.

In one implementation, control unit 62 may prompt, through display 60, a caretaker or physician to enter or adjust the value for such trigger sensitivity thresholds through input 58. As a result, the physician or caretaker may customize such threshold levels, moving such threshold lines 302 towards and away from the origin. In yet other implementations, such threshold indications may be omitted.

The spacing of a breath pair mark from quadrant bisecting line 306 within quadrant 1 may indicate that a breath initiated by patient 13 was completely missed by ventilator 12. In other words, patient 13 started to inhale, initiating a breath, but such inhalation was not sensed by ventilator 12 and no assistance (pressurized gas or air) was provided by ventilator 12. In some instances, assistance may be provided by ventilator 12, but wherein such assistance is offered extremely late or early; the firing of ventilator 12 kicking in based upon the predefined lapse of time since the last firing and not in response to the initiation of the breath by patient.

In one implementation, control unit 62 may further generate control signals causing display 60 to visibly present on the plot of breath pair marks additional missed breath threshold lines 310 which represent thresholds above and below which a breath pair mark (and breath pair) is deemed to indicate a missed breath triggering. In other implementations, such missed breath threshold lines 310 may be omitted, wherein control unit 62 performs an internal comparison with a predefined thresholds and wherein different breath pair marks are illustrated or depicted with different characteristics depending upon their relationship to the predefined thresholds 310. For example, breath pair marks outside threshold lines 310 may have one or more of a different color, a different brightness, a different size, a different flashing or flashing frequency, a different shade and the like with respect to other breath pair marks which do not lie beyond the predefined threshold. In some implementations, lines 310 may be employed with the provision of different characteristics for different breath pair marks based on their relationship to x and y axes and thresholds 310.

In one implementation, control unit 62 may prompt, through display 60, a caretaker or physician to enter or adjust the value for such missed breath thresholds through input 58. As a result, the physician or caretaker may customize such missed breath threshold levels, moving such missed breath threshold lines 310 towards and away from the line 306. In yet other implementations, such missed breath threshold indications may be omitted.

Breath pair marks plotted in quadrant 3 visibly indicate ventilator initiated breathing, wherein a ventilator 12 fires and supplies pressurized air/gas to patient 13 and wherein patient 13 may be passive. Breath pair marks 301 plotted in quadrants 2 and 4 visibly indicate a chaotic triggering or circumstances where the patient 13 is fighting ventilator 12. In the example illustrated, control unit 62 visibly displays all four quadrants for visual inspection. In other implementations, control unit 62 may alternatively display only selected quadrants, such as quadrant 1 representing stable triggering and quadrant 3 indicating a passive patient. Although breath pair marks in different quadrants are illustrated as having different visible characteristics, such as different shapes, in other implementations, breath pair marks may have the same shape or other visible characteristics regardless of which quadrant the breath pair mark 301 lies.

In one implementation, control unit 62 displays a predefined number of consecutive breath pair marks 301. For example, one implementation, control unit 62 displays 100 breath pair marks 301, removing old breath pair marks 301 on a first in-first out basis. In one implementation, control unit 62 prompts a caretaker or physician for input allowing adjustment of the number of breath pair marks 301 that are concurrently displayed on display 60. In one implementation, control unit 62 further graphically or visibly indicates the aging of breath pair marks 301 corresponding the age of the particular data pointing reflected in the plotting of FIG. 6. Such aging may be graphically depicted with different characteristics depending upon their age are certain age thresholds. For example, breath pair marks older than a first aid threshold may have one or more of a different color, a different brightness, a different size, a different flashing or flashing frequency, a different shade and the like with respect to other breath pair marks which do not fall within a certain age range or between certain age thresholds. In yet other implementations, the depiction of breath pair mark aging may be omitted. In each of the implementations where marks 301 are provided with different visible characteristics to indicate relationships with respect to sensitivity, missed breath or age thresholds, control unit 62 may prompt a caretaker or physician with an option to select the particular visible characteristic differentiation technique used, allowing the physician or caretaker to customize the display for his or her preferences.

As indicated by the remainder of method 200 and FIG. 5, control unit 62 may internally analyze the plotting of breath pair marks and may visibly present textual information based upon the plotted location of the breath pair marks. As a result, the meaning associated with the particular location of the breath pair marks is evident even to those physicians or caretakers unfamiliar with the synchrony display technique shown in FIG. 6. As indicated by step 204, controller 62 determines whether a particular breath pair mark 301 lies outside of a missed breath threshold (depicted by line 310 in the display of FIG. 6). As indicated by step 206, if controller 62 determines that a particular breath pair mark lies outside the missed breath threshold, control unit 62 generates control signals causing display 60 to specifically indicate the missed breath. The specific indication of a missed breath may be made using a graphic or icon known to indicate that a missed breath has occurred or may be achieved with an appropriate textual message, such as "missed breath".

As indicated by step 210, if control unit 62 determines that a particular breath pair mark 301 is within the missed breath thresholds, control unit 62 determines whether a particular breath pair mark 301 is still outside a trigger sensitivity threshold (depicted by one of lines 302 in the display of FIG. 6). As indicated by step 212, if control unit 62 determines that the particular breath pair mark 301 is outside a particular sensitively threshold, control unit 62 generates control signals causing display 42 specifically indicate or recommend that the sensitivity of the trigger of ventilator 12 should be adjusted. The specific indication of the need for an adjustment to ventilator trigger sensitivity may be made using a graphic or icon known to indicate an adjustment to trigger sensitivity should be made or may be achieved with appropriate textual message such as "adjustment of trigger recommended". In some implementations, the specific indication may further or additionally indicate the direction and/or the extent of adjustment that is recommended. For example, control unit 62 may compare the location of the breath pair mark 301 to several different threshold levels and generate a different adjustment recommendation depending upon which of the pressure levels is exceeded by the location of the breath pair mark 301 (or the values associated with the breath pair mark 301).

As indicated by step 220, control unit 62 further identifies the particular quadrant in which a particular breath mark 301 is located using the plot location or the corresponding values of the particular breath mark. As indicated in step 222, if control unit 62 determines that a particular breath mark is in quadrant 1, control unit 62 generates control signals causing display 60 to specifically indicate that ventilator triggering a stable for that breath mark. Such an indication may be made using a graphic or icon known to the physician or caretaker to indicate stable triggering or may be achieved with appropriate textual message such as "stable triggering".

As indicated by step 224, if control unit 62 determines that a particular breath mark is in quadrant 3, control unit 62 generates control signals causing display 60 to specifically indicate a passive patient. Such an indication may be made using a graphic or icon known to the physician or caretaker to indicate a passive patient or may be achieved with appropriate textual message such as "passive patient".

As indicated by step 226, if control unit 62 determines that a particular breath mark is in quadrant 4, control unit 62 generates control signals causing display 60 to specifically indicate a chaotic breathing or patient fighting. Such an indication may be made using a graphic or icon known to the physician or caretaker to indicate a chaotic breathing or patient fighting or may be achieved with appropriate textual message such as "chaotic breathing" or "fighting patient". In one implementation, such messages as discussed with respect to step 222, 224 226 may be streamed on display 60. In other implementations, such messages may be displayed in other fashions.

In some implementations, control unit 62 may output any of the messages identified with regard to steps 222, 224 226 only at predefined time periods or intervals and may select which of the messages is indicated based upon a statistical analysis of the number of breath pair marks falling within each of the quadrants. For example, control unit 62 may be programmed or configured to only output such a message every 30 seconds, wherein the time interval may be selectively adjustable by caretaker or physician through input 38. Control unit 62 may be programmed or configured to only indicate stable triggering (per step 222) when a predefined percentage or number of breath pair marks falls within the first quadrant. Likewise, control unit 62 may be programmed or configured to only indicate a passive patient (per step 224) or to indicate chaotic breathing or fighting up and per step 226) when a predefined percentage or number of breath marks falls within the third quadrant or within the second or fourth quadrant, respectively. The predefined threshold for the number or percentage of breath marks falling within a particular quadrant or quadrants at which such messages are displayed may be selectively adjusted by caretaker or physician through input 58. In certain circumstances, the severity of a passive patient may justify use of a lower threshold number or percentage of breath marks to trigger the display of the passive patient message or warning. In the example illustrated, the messages possibly provided through steps 204-226 occur concurrently with the presentation of display 300 in FIG. 6. In other implementations, such messages may be presented on display 60, wherein display 300 is not presented. In some implementations, the physician or caretaker may selectively choose, through input 58, whether one or both of the messages of steps 204-226 or the plotting of breath pair marks 301 per step 202 as exemplified in display 300 are presented.

In the example illustrated, the dis-synchrony between ventilator firing and initiation of a breath by a patient is graphically displayed or messages or warnings are presented based upon such dis-synchrony. In other implementations, other relationships between ventilator operation in patient breathing may be visually depicted in a similar manner. For example, instead of providing a graphical display based upon a phase angle relationship between the firing of a ventilator and airflow into the patient (the initiation of breath by patient in some circumstances), control unit 62 may alternatively or additionally provide a graphical display based upon a phase angle relationship between the cessation of ventilator assistance and airflow corresponding to exhalation by the patient. In such an alternative implementation, the phase angle for a particular breath exhalation would be calculated wherein a cycle or Ttot' of 2 Pi radians is defined by the time between consecutive ventilator drops or sensations in line 152 (shown in FIG. 3). In other implementations, the cycle may be derived from other values. For example, the cycle used for the calculation of an exhalation phase angle may alternatively comprise Ttot. In other implementations, other values may be used for the cycle for calculating a breath phase angle. The phase angle for an individual exhalation is determined according to the equation: phase angle (exhalation)=2 Pi(T2'−T1')/Ttot', where time T2' is the time at which ventilator 12 is cessated or stopped (represented by the steep downward trend in line 152 of FIG. 3) and where time T1' is a time at which a patient begins to exhale following a breath (represented by the negative or downward spike in line 154 of FIG. 3). As with display 300 and FIG. 6, the exhalation phase angles for two consecutive exhalation pairs (exhalations following two breaths) would be used to define y and x coordinates for an exhalation pair mark.

In such an alternative implementation, control unit 62 plots consecutive exhalation pair marks. A calculated phase angle for a first exhalation of a consecutive pair of exhalations determines the y-axis coordinate or value for the exhalation pair mark and the calculated phase angle for a second exhalation of the consecutive pair of exhalations determines the x-axis coordinate or value for the exhalation pair mark. A first exhalation having a positive phase angle and a second exhalation also having a positive phase angle, forming a first pair of exhalations, will result in the plotting of a first mark in quadrant 1. A third exhalation having a negative calculated phase angle, forming a second exhalation pair with the second exhalation, will result in the plotting of a second mark in quadrant 2. A fourth exhalation having a negative calculated phase angle, forming a third exhalation pair with the third exhalation, will result in the plotting of a third exhalation mark in quadrant 3. A fifth exhalation having a positive calculated phase angle and forming a fourth pair with the fourth exhalation result in the plotting of a fourth mark in quadrant 4. Each exhalation forms the y-axis coordinate for a first exhalation pair mark and the x-axis coordinate for a second exhalation pair mark.

In one implementation, the plotting of exhalation pair marks (similar to as shown in FIG. 6) is presented on display 60 by control unit 62. Visual inspection of the quadrant in which a particular exhalation pair mark lies as well as its relationship to the origin (x=0, y=0) provides the caretaker or physician with immediate information as to the synchrony or dis-synchrony between patient exhalation and ventilator pauses.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An apparatus comprising:
a display; and
a processing unit to receive a first input based on airflow in a ventilator for a breath and a second input based upon ventilator firing for the breath, wherein the processing unit is configured to determine a phase angle based on a relationship between the first input and the second input and to provide an indication on the display of a nature of dis-synchrony of airflow and ventilator firing based on the phase angle, wherein the indication comprises a visual depiction of a phase angle relationship between successive breaths and wherein the visual depiction comprises a graphical plotting of the phase angle relationship of successive breath pairs with respect to an origin and x and y axes intersecting one another at the origin, the graphical plotting comprises a plurality of breath pair markings, each marking having an x-coordinate value starting from the origin based upon the phase angle of one of the successive breaths and a y-coordinate value starting from the origin based upon the phase angle of the other of the successive breaths.

2. The apparatus of claim 1, wherein the processing unit is further configured to visually depict thresholds above and below which a breath pair is deemed to indicate a missed breath triggering.

3. The apparatus of claim 2 further comprising an input to the processing unit, wherein the thresholds are adjustable in response to selections provided to the input.

4. The apparatus of claim 1, wherein the processing unit is further configured to provide a visual indication of an age of each breath pair mark.

5. The apparatus of claim 1, wherein the processing unit is further configured to visually depict a threshold with respect to the origin beyond which a breath pair mark is deemed to suggest the adjustment of ventilator trigger sensitivity.

6. The apparatus of claim 1, wherein the processing unit is configured to indicate a chaotic breathing characteristic or a patient fighting the ventilator characteristic in response to a phase angle relationship between successive breaths falling into either a second quadrant or a fourth quadrant.

7. The apparatus of claim 1, wherein the processing unit is configured to indicate a passive patient characteristic in response to a phase angle relationship of successive breaths falling in a third quadrant.

8. The apparatus of claim 1, wherein the processing unit is configured to provide a suggestion for trigger sensitivity adjustment in response to a phase angle relationship of successive breaths lying beyond a predetermined distance from an origin.

9. A method comprising:
for each of a plurality of breaths, determining a phase angle between a first signal based on ventilator airflow for a breath and a second signal based upon ventilator firing for the breath; and
providing an indication of a nature of dis-synchrony of airflow and ventilator firing based on the phase angle, wherein the indication comprise a visual depiction of a phase angle relationship between successive breaths, and wherein the visual depiction comprises a graphical plotting of the phase angle relationship of successive breath pairs with respect to an origin and x and y axes intersecting one another at the origin, the graphical plotting comprises a plurality of breath pair markings, each marking having an x-coordinate value starting from the origin based upon the phase angle of one of the successive breaths and a y-coordinate value starting from the origin based upon the phase angle of the other of the successive breaths.

10. The method of claim 9 further comprising visually depicting thresholds above and below which a breath pair is deemed to indicate a missed breath triggering.

11. The method of claim 10 further comprising adjusting the thresholds.

12. The method of claim 9 further comprising visually indicating an age of each breath pair mark.

13. The method of claim 9 further comprising visually depicting a threshold with respect to the origin beyond which a breath pair mark is deemed to suggest the adjustment of ventilator trigger sensitivity.

14. The method of claim 9 comprising indicating a chaotic breathing characteristic or a patient fighting the ventilator characteristic in response to a phase angle relationship between successive breaths falling into either a second quadrant or a fourth quadrant.

15. The method of claim 9 comprising indicating a passive patient characteristic in response to a phase angle relationship of successive breaths falling in a third quadrant.

16. The method of claim 9 comprising indicating a suggestion for trigger sensitivity adjustment in response to a phase angle relationship of successive breaths lying beyond a predetermined distance from an origin.

17. An apparatus comprising:
a non-transient computer-readable medium comprising code to direct a processing unit to:
to receive a first input based on airflow in a ventilator for a breath;
to receive a second input based upon ventilator firing for the breath;
to determine a phase angle based on a relationship between the first input and the second input; and
to provide an indication on a display of a nature of dis-synchrony of the first input and the second input based on the phase angle, wherein the indication comprises a visual depiction of a phase angle relationship between successive breaths and wherein the visual depiction comprises a graphical plotting of the phase angle relationship of successive breath pairs with respect to an origin and x and y axes intersecting one another at the origin, the graphical plotting comprises a plurality of breath pair markings, each marking having an x-coordinate value starting from the origin based upon the phase angle of one of the successive breaths and a y-coordinate value starting from the origin based upon the phase angle of the other of the successive breaths.

* * * * *